US00PP10630P

United States Patent [19]

Saville

[11] Patent Number: Plant 10,630

[45] Date of Patent: Oct. 6, 1998

[54] MINIATURE ROSE PLANT NAMED 'SAVAJERRY'

[75] Inventor: F. Harmon Saville, deceased, late of Newburyport, Mass., by Charles K. Brown, executor

[73] Assignee: Nor'East Miniature Roses, Inc., Rowley, Mass.

[21] Appl. No.: 950,937

[22] Filed: Oct. 15, 1997

[51] Int. Cl.[6] ..... A01H 5/00

[52] U.S. Cl. ..... Plt./10

[58] Field of Search ..... Plt./7.1, 10, 9, Plt./10.1

*Primary Examiner*—Howard J. Locker

*Attorney, Agent, or Firm*—Christie, Parker & Hale, LLP

[57] ABSTRACT

A new miniature rose with light red flowers.

1 Drawing Sheet

BACKGROUND OF THE INVENTION

The present invention relates to a new and distinct variety of rose plant of the miniature rose class, which was created by crossing as seed parent the variety known as 'Lavjune' (U.S. Plant Pat. No. 6,859) and as pollen parent the variety known as 'Savasach' (U.S. Plant Pat. No. 5,967). The varietal denomination of this new rose is 'Savajerry'.

SUMMARY OF THE INVENTION

Among the novel characteristics possessed by this new variety which distinguishes it from its parents and all other varieties of which I am aware is its attractive light red flowers borne on a plant with a growth habit suitable for use in a perennial garden.

Asexual reproduction by propagation of vegetative cuttings of the new variety as performed in Essex County, Massachusetts shows that the foregoing and other distinguishing characteristics come true to form and are established and transmitted through succeeding propagations.

COMPARISON WITH PARENTS

The new variety differs from its parents in flower color.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

Parentage:

*Seed parent.*—'Lavjune'.

*Pollen parent.*—'Savasach'.

Class: Miniature.

The following observations are made of specimens grown under plastic in Essex County, Mass., during October.

Flower

Blooming habit: Continuous.

A. Bud:

(1) *Size.*—Medium.

(2) *Form.*—Obtuse with acute tip.

(3) *Color.*—As sepals divide, bud color is near 46B.

(4) *Sepals.*—Very slightly bearded; lanceolate; about 3/16 inch longer than the bud; color between near 144B and 146C; sepals bend back to stem and occasionally cross over; as hips mature sepals start to uncurl but die and drop off before returning to original upright position (before hips fully mature).

(5) *Peduncle.*—Length — about 11/16 inch. Aspect — slightly curved. Strength — erect. Color — near 144C occasionally flushed with near 185B.

B. Bloom:

(1) *Size.*—Average size when fully expanded up to about 2½ inches.

(2) *Borne.*—Singly in small clusters.

(3) *Form.*—Bud opens slowly then opens to near flat with petals loosely rolled outward.

(4) *Petalage.*—Number of petals under normal conditions about 16–20.

(5) *Color.*—When petals begin to unfurl, near 46C; ½ open — near 45C on top and near 45D on underside of outer petals, near 46B and 45B, respectively on the top and underside of inner petals, base petals at point of attachment near 17B; general tonality from a distance medium red.

(6) *Color change.*—As bloom ages, color changes from near 46B, to 46B and 45C and 45D to near 53D and remaining so until petals fall; after three or more days general tonality is medium to light red.

C. Petals:

(1) *Texture.*—Moderately thick.

(2) *Appearance.*—Outside satiny, inside matte.

(3) *Form.*—Broad fan shaped.

(4) *Arrangement.*—Imbricated, regularly arranged, shingle-like.

(5) *Petaloids in center.*—0–2, occasionally light yellow streak.

(6) *Persistence.*—Drop off cleanly in 4–7 days.

(7) *Fragrance.*—Strong old rose.

(8) *Lasting quality.*—About 4–7 days on the plant; about 5–9 days as a cut flower.

Reproductive Organs

A. Stamens, filaments and anthers:

*Arrangement.*—Loosely arranged around styles.

B. *Stamens*:
*Quantity.*—Many.
C. Filaments:
*Approximate length.*—About 3/16 inch to 3/8 inch.
*General color.*—Near 12B to near 12D, some near 12D with light red tint.
D. Anthers:
*Color.*—Near 14D.
E. Pollen
*Color.*—Near 21B.
*Quantity.*—Great/large amount.
F. Pistils:
*Quantity.*—Many.
G. Styles: Uneven
*Color.*—Near 1D, up to about 1/16 inch, packed tightly together in center of flower.
H. Stigmas:
*Color.*—Near 1D.
I. Hips:
*Shape.*—Globular.
*Size.*—About ½ inch to ¾ inch in diameter.
*Seeds.*—Seed do not protrude.
*Color.*—Near 46A on a side and near 24A on other side blending together in between.

Plant

A. Form: Upright and spreading.
Growth: Well branched.
*Height.*—About 18 to 22 inches high and about 30 inches spread.
*Length of flowering stem:*—Varying in length up to about 5 inches.
C. Foliage: Compound of 5–7 leaflets, occasional 3 or 9.
*Size.*—Medium.
*Quantity.*—Abundant.
*Color.*—New Foliage: Upper side near 137B with serrated tips near 184B; under side near 147C flushed slightly with near 184D. Old Foliage: Upper side near 147A; under side near 147B.
*Shape.*—Usually oval, pointed, occasionally oval with no point.
*Texture.*—Upper side matte; underside matte.
*Thorns or prickles.*—Usually up to about 1 to 3 prickles on underside of leaf stem.
*Edge.*—Serrated.
*Serration.*—Fine, uneven.
*Leaf stem.*—Near 146B underside near 144A.
*Stipules.*—Slightly serrated.
*Resistance to diseases.*—Blackspot: Average. Mildew: Average. Rust: Average.
D. Wood:
*New wood.*—Color between 146B and 144B flushed with near 184A; bark smooth.
*Old wood.*—Color near 144B; bark has slightly raised areas of near 175A.
E. Thorns:
*Quantity.*—Many on main stalk and laterals.
*Form.*—Usually straight, occasionally curve upward.
*Length.*—Short.
*Color.*—Near 185C when young.
*Position.*—Very irregular.
F. Prickles:
*Main stalk.*Some.
*Laterals.*—Some.
*Leaves.*—Usually about 1 to 3 prickles on underside of leaf stems.
G. Winter hardiness: Needs protection in severe climate.

I claim:

1. A new and distinct variety of rose plant of the miniature rose class, substantially as shown and described.

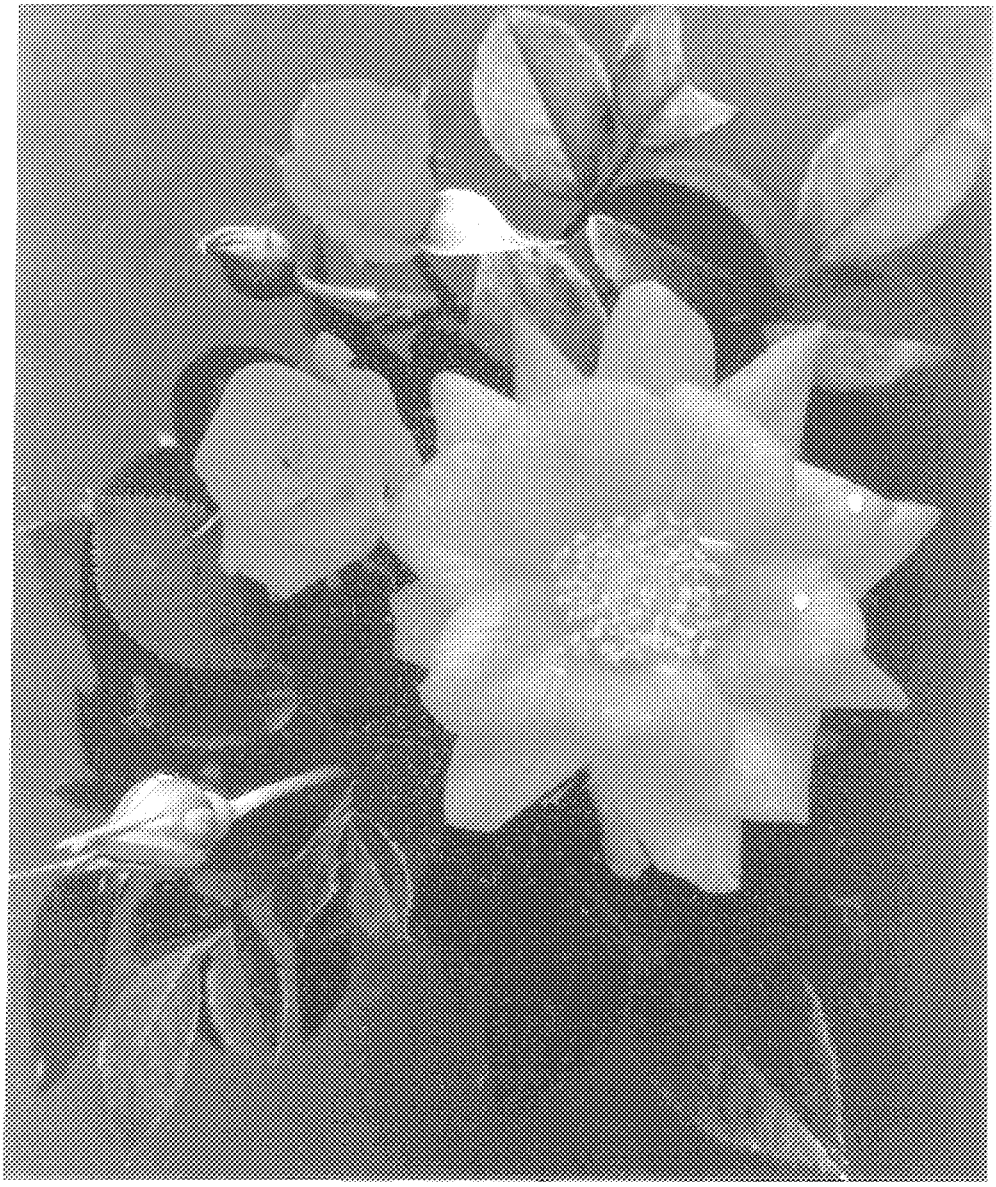

* * * * *